United States Patent [19]

Lagneaux et al.

[11] Patent Number: 5,480,591
[45] Date of Patent: Jan. 2, 1996

[54] DYNAMIC DIFFUSER OF A SUBSTANCE SUCH AS A PERFUME

[75] Inventors: Patrick Lagneaux, Onnaing; Christian Peretti, Valenciennes, both of France

[73] Assignee: Prodifa (S.A.R.L.), France

[21] Appl. No.: 404,529

[22] Filed: Mar. 15, 1995

[30] Foreign Application Priority Data

Mar. 16, 1994 [FR] France .................. 94 03304

[51] Int. Cl.⁶ .................. B01F 3/04
[52] U.S. Cl. .................. 261/30; 261/84; 261/104; 261/DIG. 65; 422/124
[58] Field of Search .................. 261/30, 84, 104, 261/83, DIG. 65

[56] References Cited

U.S. PATENT DOCUMENTS

| 2,720,013 | 10/1955 | Clarke | 21/126 |
|---|---|---|---|
| 3,618,911 | 11/1971 | Martin et al. | 261/104 |
| 4,035,451 | 7/1977 | Tringall | 261/101 |
| 4,157,787 | 6/1979 | Schwartz | 239/56 |
| 4,356,969 | 11/1982 | Obermayer et al. | 239/6 |
| 4,383,951 | 5/1983 | Palson | 261/30 |
| 4,944,898 | 7/1990 | Glaser | 261/84 |
| 5,230,837 | 7/1993 | Babasade | 261/30 |

FOREIGN PATENT DOCUMENTS

| 1174101 | 9/1984 | Canada | A61L 9/04 |
|---|---|---|---|
| 1454040 | 10/1976 | United Kingdom | A61L 9/04 |
| 2194889 | 3/1988 | United Kingdom | A61L 9/04 |
| 8100051 | 1/1981 | WIPO | A61L 9/04 |
| 9406480 | 3/1994 | WIPO | A61L 9/04 |

Primary Examiner—Tim R. Miles
Attorney, Agent, or Firm—Ladas & Parry

[57] ABSTRACT

The dynamic diffuser for a naturally diffusing liquid substance such as a perfume comprises a receptacle for said substance and having a vertical flank which is closed by a membrane that is impermeable to liquid but permeable to gas. All or part of the membrane is caused to come into contact with said substance, at least intermittently, by revolving the receptacle about a horizontal axis. Air-flow generating means, e.g. impeller blades, serve to cause air to flow over the outside of the membrane.

8 Claims, 3 Drawing Sheets

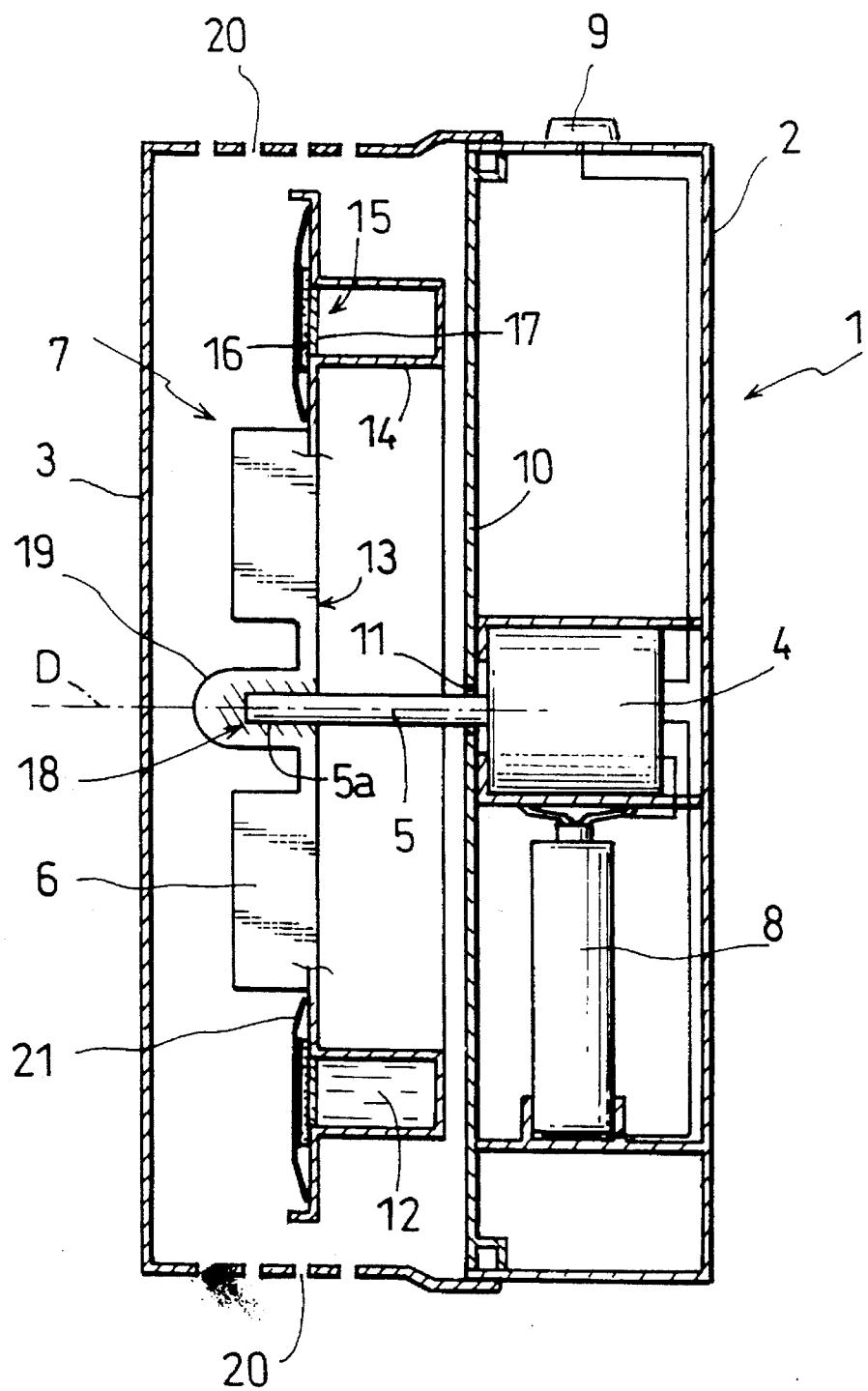
FIG_1

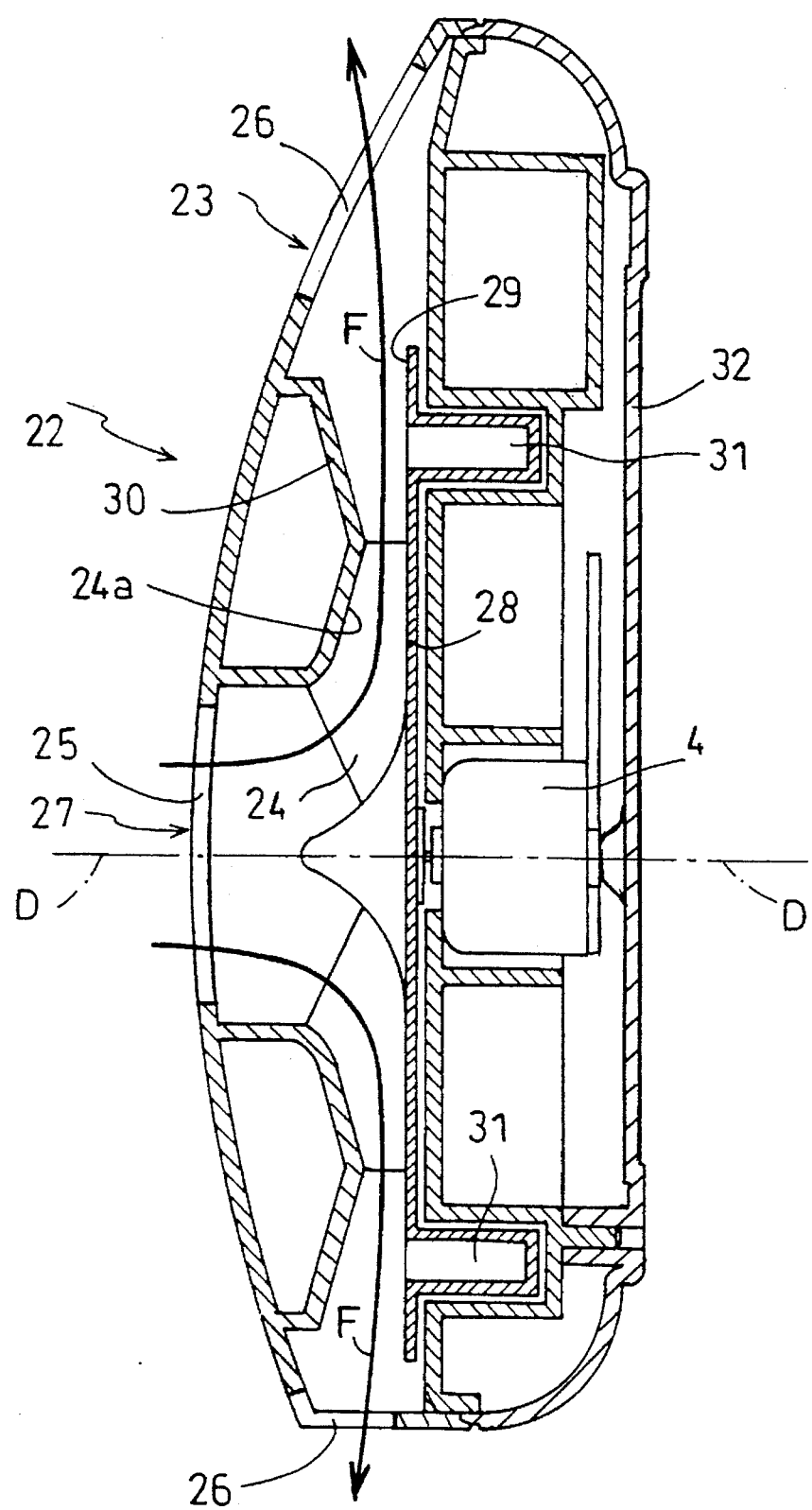
FIG_2

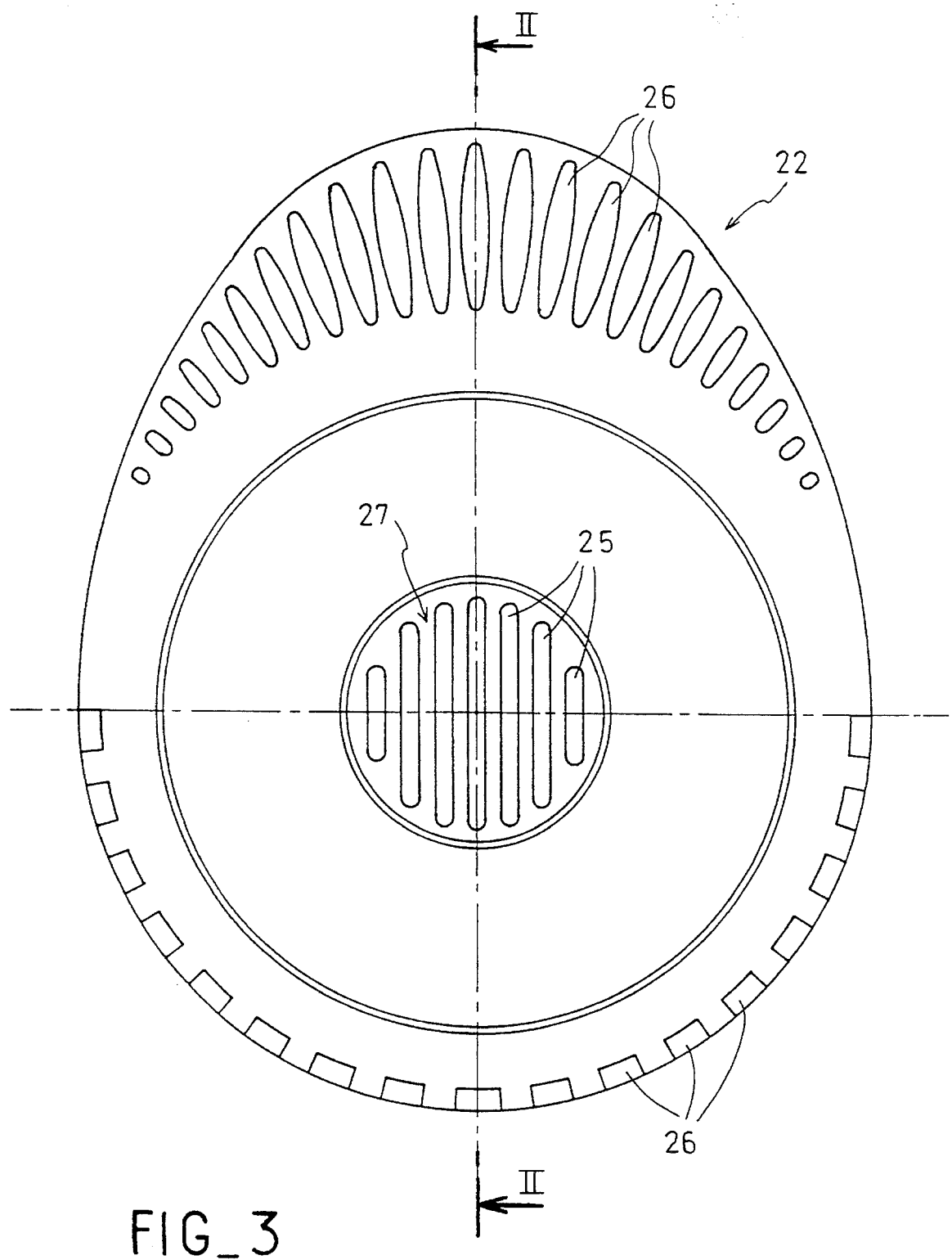
FIG_3

DYNAMIC DIFFUSER OF A SUBSTANCE SUCH AS A PERFUME

FIELD OF THE INVENTION

The present invention relates to a perfume diffuser or more generally a diffuser of a substance that diffuses naturally in the atmosphere, e.g. deodorizer, insecticide, germicide, ... . More particularly, the invention relates to a dynamic diffuser for such substances, i.e. a diffuser which is provided with airflow generating means to enhance the natural diffusion of the substance and its delivery into the surrounding atmosphere.

BACKGROUND OF THE INVENTION

Document FR-2-358 897 discloses a dynamic diffuser which comprises, in a housing provided with air evacuation orifices, a fan enabling a flow of air to be passed over the medium supporting the substance to be vaporized.

In a preferred embodiment described in that prior document, the dynamic diffuser includes a removable cartridge which is constituted firstly by a round battery for electrically powering a motor which drives the fan, and secondly an annular receptacle mounted around said round battery and containing the material supporting the substance to be vaporized. Said annular receptacle is pierced in its two plane faces by orifices for passing air. The cylindrical cartridge is placed coaxially relative to the axis of rotation of the fan and it faces the fan so that the air flow created by rotation of the fan penetrates into the receptacle, travels over the surface of the medium supporting the substance to be vaporized, and escapes from the housing. In that case, the medium supporting the substance to be vaporized is a porous strip impregnated with said substance.

In the field of perfume, dynamic diffusers of that type are also known in which the perfume element is in the state of a gel or of a solid block. The flow of air coming from a fan and travelling over the surface of the gel or the block accelerates natural diffusion of the perfume.

As observed by the Applicant, such known dynamic diffusers suffer from a drawback which consists in the concentration of the perfumed substance in air diminishing progressively over time. Thus, in a room containing the diffuser in question, a user does not obtain the same perfume sensation throughout the time during which the diffuser is in use.

If the substance to be vaporized is an insecticide, then the effectiveness of the diffuser decreases over time.

Proposals have already been made in document GB-1-454 040 for a diffuser in which the naturally diffusing substance is in the liquid state. The diffuser in question includes a receptacle whose bottom is pierced by an orifice which leads to a chamber containing an absorbent material. The liquid passes progressively into the absorbent material under gravity and under capillarity. The chamber is itself provided with lateral openings, and a fan is disposed facing said openings so that a flow of air passes through the chamber and the absorbent pad, and becomes charged with the naturally diffusing substance.

The Applicant has found that that diffuser suffers from drawbacks. When the absorbent material is saturated, the liquid substance drips out from the chamber and is lost. The flow of air through the absorbent material suffers a large loss of head, thereby requiring greater power for the fan-driving motor for a given air flow. The chamber containing the absorbent material is bulky.

OBJECT AND SUMMARY OF THE INVENTION

The object of the Applicant is to provide an improved dynamic diffuser that mitigates the abovementioned drawbacks.

The diffuser is a diffuser for a naturally-diffusing liquid substance such as a perfume, the diffuser including a receptacle for said liquid substance and air-flow generating means situated in the diffusion zone. In characteristic manner, the receptacle is closed by a membrane that is impermeable to liquid and that is permeable to gas; at least a portion of said membrane constitutes a vertical flank of the receptacle; in addition, the diffuser includes means for displacing the receptacle suitable for causing the receptacle to revolve about a horizontal axis, thereby putting the liquid substance at least intermittently into contact with the membrane constituting said vertical flank.

While the receptacle is revolving, the liquid it contains is always in contact with at least a portion of the vertical flank constituted by the membrane, regardless of the quantity of liquid substance that is still to be found in the receptacle. Thus, the motion of the receptacle makes it possible to moisten the membrane constantly, even after prolonged use has reduced the quantity of liquid in the receptacle.

The membrane that is impermeable to liquid and permeable to gas is a porous membrane whose pores are of an appropriate size to pass a flow of gas while preventing liquid from passing. This type of membrane is known and is constituted, in particular, of polypropylene. Advantageously, the inside face of said membrane is coated in an absorbent material. This is to obtain controlled diffusion while ensuring that the absorbent material which is in contact with the membrane is kept constantly moist.

The receptacle is preferably annular in shape and the air-flow generating means are placed at the central opening of said receptacle in a manner such that the flow of air generated by said air-flow generating means takes place over the entire area of the vertical flank constituted by the membrane, going outwards from said central opening.

Advantageously, in the same disposition, the airflow generating means are constituted by a impeller which is mounted on a rotary circular plate having the annular receptacle fixed at its periphery, the membrane being disposed radially relative to the direction in which air is delivered by the impeller during rotation of the plate.

Thus, in this preferred embodiment of the invention, when the receptacle is caused to rotate, the membrane is simultaneously continuously moistened by using the same means as are used for generating the flow of air.

Advantageously, the diffuser of the invention includes an outer body that serves as a housing for the set of elements constituting said diffuser, namely the annular receptacle, the circular plate provided with the impeller, and the means for rotating said plate; in addition, the outer body is pierced by two sets of openings, a first set which is in a zone situated close to the axis of rotation of the plate and facing the impeller, and a second set which is in a zone offset radially relative to said plate. In this way, a flow of air is generated which penetrates into the outer body via the first set of openings and which leaves the body via the second set. This flow of air necessarily passes over the surface of the annular membrane which covers the receptacle disposed at the periphery of the circular plate.

In this case, the outer body preferably includes an internal annular shoulder which separates the two sets of openings and which lies flush with the top surface of the impeller while the circular plate is revolving. This particular disposition provides the advantage of defining an unavoidable passage between the first and second sets of openings for the flow of air, which passage has the blades of the impeller moving therethrough while the impeller is rotating. The air flow is thus generated much more efficiently by a turbine effect.

The invention also provides a self-contained cartridge designed to be incorporated in the abovespecified dynamic diffuser of a substance, and in particular of a perfume. In characteristic manner, said cartridge is constituted by:

a) a circular plate including, on its axis of rotation, means for coupling to the shaft of a motor suitable for causing said plate to revolve, and also including, on one of its faces, blades for generating a flow of air;

b) a receptacle for the liquid substance to be diffused, which receptacle is constituted by an annular hollow body having an open face and disposed at the periphery of the circular plate in such a manner that the open face is substantially flush with said plate;

c) a membrane that is impermeable to liquid and permeable to gas, which membrane is fixed at the periphery of the plate over the open face of the hollow body after the liquid substance to be diffused has been placed therein; and d) a closure film that is impermeable to liquid and to gas, and that is fixed on the periphery of the plate so as to cover said membrane.

Thus, a user possessing the above-described diffuser need only remove the closure film which has so far prevented any substance being diffused, and then place the cartridge inside the diffuser so that the shaft of the drive motor contained in said diffuser couples so as to drive the circular plate.

Preferably, in a variant embodiment of a diffuser having an outer body, said body is constituted by a housing to which there are fixed the rotary drive means for the cartridge plus a cover provided with the two sets of openings and the internal annular shoulder. Once the cartridge has been placed inside the housing, the user need only close the cover in order to create the abovementioned turbine effect.

BRIEF DESCRIPTION OF THE DRAWINGS

The present invention will be better understood on reading the following description of a preferred embodiment of the dynamic diffuser of liquid perfume, as illustrated in the accompanying drawings, in which:

FIG. 1 is a diagrammatic section view through a first variant of a dynamic diffuser for liquid perfume;

FIG. 2 is a diagrammatic section view through a second variant of a dynamic diffuser; and FIG. 3 is a plan view from above of the second variant diffuser.

MORE DETAILED DESCRIPTION

The object of the device of the invention is to diffuse a substance such as a perfume, a deodorizer, an insecticide, or any other substance that it is desired to spread through the atmosphere in a room. More specifically, the device makes use of diffusion that is dynamic in the sense that natural diffusion is combined with a flow of air.

In the example shown in FIG. 1, the device is a dynamic diffuser 1 for perfume that is in the liquid state.

The diffuser 1 comprises a housing 2 that is closed by a cover 3 containing both elements for generating a flow of air and also elements enabling the liquid perfume to be diffused.

The air-flow generating elements are constituted by a motor 4 whose body is fixed laterally in the middle portion of the housing 2 and whose rotary shaft 5 lies axially inside the cover 3, and also a impeller 6 that forms a portion of a removable cartridge 7 that is described below.

The motor 4 is powered by a battery 8 received in the housing 2, and it is controlled by a switch 9 placed on the outside of the housing 2. Naturally, the switch could be placed inside the housing for reasons of appearance or to prevent unwanted use by a non-authorized person.

The housing 2 is closed by a closure plate 10 that is engageable on the housing 2 and that includes a central orifice 11 through which the rotary shaft 5 passes.

The cartridge 7 which is designed to be rotated by the shaft 5 is a removable cartridge suitable for being discarded after use, i.e. once all of the perfume 12 in the liquid state has been diffused.

The cartridge 7 comprises a circular plate 13 having mounted thereon both the receptacle 14 containing the perfume 12 in the liquid state and the impeller 6.

The impeller 6 is made up of blades extending between two concentric circles about the axis of rotation D of the cartridge 7. The receptacle 14 is a hollow body of annular shape, having a cross-section that is substantially rectangular, and which is disposed on the opposite face of the plate 13 to the face carrying the impeller 6. The receptacle 14 is closed on three faces only, its open face 15 being covered by a membrane 16 that is both impermeable to liquid and permeable to gas. It may be constituted, for example, by a sheet of microporous polypropylene. The membrane 16 is fixed on the circular plate 13 on either side of the receptacle 14 by thermosealing, or by thermofusing using heat or ultrasound. The thermofusing may be performed under a vacuum, in which case the receptacle may be filled by injection after thermofusing.

The membrane 16 is preferably coated on its inside face, i.e. its face looking into the inside of the receptacle 14, in an absorbent material 17.

As can be seen in FIG. 1, the receptacle 14 is disposed concentrically about the axis of rotation D of the cartridge 7, and outside the impeller 6.

The cartridge 7 is fitted onto the rotary shaft 5 by the end 5a of the shaft being received in a socket 18 formed in an axial thickening 19 of the plate 13.

The housing 2 and its cover 3 are preferably substantially cylindrical in shape, and the cover 3 possesses air-passing orifices 20 around its entire annular periphery.

During storage, the cartridge 7 also includes a closure film 21 which closes the membrane 16 hermetically, being fixed to the circular plate 13 on either side of said membrane 16. This sheet may be constituted, for example, by an aluminum and polyethylene composite. The polyethylene prevents any leakage of perfume in the liquid state from the receptacle 14, while the gas-impermeable aluminum prevents any loss of perfume. The film 21 is fixed in place by thermosealing or by ultrasound or heat thermofusion.

The diffuser operates as follows. The user begins by opening the cartridge 7 by removing the closure film 21 from the membrane 16. Thereafter, while the cover 3 is open, the user fits the cartridge 7 on the rotary shaft 5, engaging the free end 5a in the socket 18 which is appropriately shaped to receive said end 5a of the shaft 5.

The cartridge 7 is then ready for use and the user can close the cover 3. By using a switch 9, the user turns on the motor 4, thereby causing the shaft 5 to rotate. The cartridge 7 then revolves about the horizontal axis D.

As the cartridge revolves, the perfume 12 in the liquid state contained in the housing 14 is kept constantly in contact with the membrane 16 that is impermeable to liquid and that is permeable to gas, which membrane constitutes one of the side flanks of the housing 14. Because of this permanent contact, the perfume can diffuse naturally through the membrane 16.

In addition, while the cartridge 7 is revolving, the impeller 6 causes air to be moved away from the axis D towards the periphery of the plate 13. The disposition whereby the impeller 6 is constituted by blades extending between two concentric circles makes it possible to achieve uniform and continuous motion of air over the entire periphery of the impeller, thereby generating a flow that sweeps over the zone situated facing the outside surface of the membrane 16, i.e. the zone in which the perfume from the receptacle 14 diffuses naturally. The flow of air passing through this zone is expelled through the orifices 20 situated at the periphery of the cover 3 and is applied dynamically to the premises which is to be perfumed.

Naturally, while the diffuser 1 is in use, the amount of perfume 12 in the liquid state inside the receptacle 14 diminishes because said perfume has evaporated. As the amount of perfume diminishes, the level of the liquid 12 inside the housing 14 drops, such that progressively only the portion of the membrane 16 that is situated at any given instant at the bottom of the cartridge 7 is actually in contact with the perfume 12 in the liquid state. However, on each rotation of the housing 14, all of the membrane 16 moves past the remaining liquid so it is always more or less impregnated with perfume 12 in the liquid state. Such impregnation is enhanced by the absorbent material 17 covering the inside surface of the membrane 16.

It is thus possible to use all of the liquid perfume 12 contained in the receptacle 14 while ensuring uniform and continuous diffusion of the perfume into the atmosphere.

As a function of the volume of the premises to be perfumed, it is possible to provide suitably adapted diffusers in which the speed of rotation of the shaft 5, the height, and the size of the blades 6 are a function of the flow of air to be set into motion, or indeed it is possible to provide for rotation to be controlled in appropriate cycles by means of an electronics module.

The diffuser 1 as described above is powered by a battery, e.g. a 1.5-volt battery or a 9-volt battery, however it is possible to provide for it to be powered by solar cells, thereby making it possible to avoid the drawbacks associated with using batteries in public places. When the motor is powered by solar cells, the rotation of the motor can be regulated on a continuous basis by masking the solar cells to a greater or lesser extent.

A second embodiment of the diffuser 22 is shown in FIGS. 2 and 3.

The diffuser 22 differs from the first embodiment mainly by the structure of its cover 23 and by the structure of its impeller 24.

As can be seen clearly in FIG. 3, the cover 23 has two sets of openings 25, 26. The first set of openings 25 is pierced through the cover 23 in a zone 27 that is situated substantially on the axis of rotation D of the cartridge 28.

The second set of openings 26 is situated in a zone that extends substantially all around said cover 23 and which is disposed radially relative to the circular plate 29 of the cartridge 28.

The cover 23 also includes an internal shoulder 30 which is annular in shape, symmetrical about the axis D, and substantially flush with the top face 24a of the impeller 24 when the impeller is rotating about the axis D.

Thus, when the cartridge 28 is revolving about the axis D, a flow of air is generated inside the cover 23 with the air inlet being through the first set of openings 25 and the air outlet being through the second set of openings 26. This flow of air is represented by arrows F in FIG. 2 and it is constrained to pass through the space through which the blades of the impeller 24 move, which space is defined between the circular plate 29 and the annular shoulder 30. This flow of air passes necessarily over the membrane (not shown) covering the annular receptacle 31 which contains the perfume. With an impeller 24 having straight blades, excellent results have been obtained concerning aerodynamic efficiency.

In the second embodiment, the diffuser 22 is no longer circular in shape but somewhat oval, the battery for powering the motor being housed in the topmost portion of the housing 32. This makes it possible to obtain a diffuser that is very compact and that has an outside shape that is pleasing in appearance, as can be seen in FIG. 3. It will be understood that in order to obtain uniform distribution of the flow of air, it is important that the area occupied by the openings 26 in the top portion of the housing should be the same as the area of the openings 26 located in the bottom portion of the same housing.

The present invention is not limited to the particular embodiments that have been described by way of non-limiting examples. In particular, it will be possible to provide the motor with a locking or sealing ring system co-operating with the female portion of the cartridge to prevent the cartridge being removed by any user not in possession of appropriate unlocking means. Provision could also be made to prevent another cartridge being fitted.

We claim:

1. A dynamic diffuser for a naturally diffusing liquid substance such as a perfume, the diffuser comprising a receptacle for the liquid substance and air-flow generating means situated in a diffusion zone, wherein the receptacle is closed by a membrane that is impermeable to liquid and permeable to gas, at least a portion of said membrane constituting a vertical flank of the receptacle, and including means for moving the receptacle so as to cause it to revolve about a horizontal axis, thereby causing the liquid substance to be put at least intermittently into contact with the membrane constituting said vertical flank.

2. A diffuser according to claim 1, wherein the inside face of the membrane constituting the vertical flank of the receptacle is covered in an absorbent material.

3. A diffuser according to claim 1, wherein the receptacle is annular in shape, and the air-flow generating means are placed at the central opening of said receptacle in such a manner that the flow of air generated by said air-flow generating means takes place over the entire area of the vertical flank constituted by the membrane, outwardly from said central opening.

4. A diffuser according to claim 3, wherein the air-flow generating means comprise an impeller mounted on a rotary circular plate, the annular receptacle being fixed at the periphery thereof, the membrane being disposed radially relative to the direction in which air is delivered by the impeller while the plate is rotating.

5. A self-contained cartridge for incorporating in the dynamic diffuser of a substance, in particular a perfume, according to claim 4, and constituted by:

a) a circular plate including, on its axis of rotation, means for coupling to the shaft of a motor suitable for causing said plate to revolve, and also including, on one of its faces, blades for generating a flow of air;

b) a receptacle for the liquid substance to be diffused, which receptacle is constituted by an annular hollow body having an open face and disposed at the periphery of the circular plate in such a manner that the open face is substantially flush with said plate;

c) a membrane that is impermeable to liquid and permeable to gas, which membrane is fixed at the periphery of the plate over the open face of the hollow body after the liquid substance to be diffused has been placed therein; and d) a closure film that is impermeable to liquid and to gas, and that is fixed on the periphery of the plate so as to cover said membrane.

6. A diffuser according to claim 4, including an outer body containing the annular receptacle, the circular plate carrying the impeller, and the means for rotating said plate, and wherein said outer body is pierced by two sets of openings, the first set being in a zone situated close to the axis of rotation of the circular plate, facing the impeller, and the second set lying in a zone situated radially relative to said plate.

7. A diffuser according to claim 6, wherein the outer body includes an internal annular shoulder separating the two sets of openings and flush with the top surface of the impeller during rotation of the plate.

8. A diffuser according to claim 7, wherein the outer body is constituted by a housing and by a cover, said cover being provided with the two sets of openings and with the internal annular shoulder.

* * * * *